United States Patent [19]

Takano et al.

[11] Patent Number: 4,688,578
[45] Date of Patent: Aug. 25, 1987

[54] ULTRASONIC PROBE DEVICE

[75] Inventors: Masayuki Takano; Kazuhumi Ishiyama, both of Ootawara, Japan

[73] Assignee: Tokyo Shibaura Denki Kabushiki Kaisha, Kawasaki, Japan

[21] Appl. No.: 590,287

[22] Filed: Mar. 16, 1984

[30] Foreign Application Priority Data

Mar. 25, 1983 [JP] Japan .......................... 58-43575[U]

[51] Int. Cl.⁴ .............................................. A61B 10/00
[52] U.S. Cl. .................................................... 128/660
[58] Field of Search ......................... 128/660, 661, 663

[56] References Cited

U.S. PATENT DOCUMENTS

| | | | |
|---|---|---|---|
| 4,059,098 | 11/1977 | Murdock | 128/660 |
| 4,154,231 | 5/1979 | Russell | 128/663 |
| 4,181,120 | 1/1980 | Kunii et al. | 128/660 |
| 4,185,502 | 1/1980 | Frank | 128/660 X |
| 4,282,880 | 8/1981 | Gardineer et al. | 128/660 |
| 4,469,106 | 9/1984 | Harui | 128/660 |
| 4,483,343 | 11/1984 | Beyer et al. | 128/660 |
| 4,491,137 | 1/1985 | Jingu | 128/660 |

FOREIGN PATENT DOCUMENTS

| | | | |
|---|---|---|---|
| 0059785 | 9/1982 | European Pat. Off. | 128/660 |
| 3337842 | 4/1984 | Fed. Rep. of Germany | 128/660 |
| 2318613 | 2/1977 | France | 128/660 |

Primary Examiner—Kyle L. Howell
Assistant Examiner—Francis J. Jaworski
Attorney, Agent, or Firm—Finnegan, Henderson, Farabow, Garrett & Dunner

[57] ABSTRACT

A probe has a step portion between its upper and lower lateral faces. A water bag has a container portion for containing water therein, and an engaging portion which is integrally formed with the container portion and which has a greater wall thickness than that of the container portion. The engaging portion is put on the upper lateral faces of the probe, with its sealing portion being pressed against the step portion. The press portion of a fitting member is caused to engage with the step portion, with the sealing portion therebetween. In this state, a clamp member clamps the fitting member, so that the sealing portion is held under pressure between the press portion and the step portion. Thus, the sealing portion is pressed against the step portion, and water poured into the water bag through a tube is contained therein in a liquid-tight manner. The probe and the object to be examined are acoustically coupled by means of the water.

7 Claims, 10 Drawing Figures

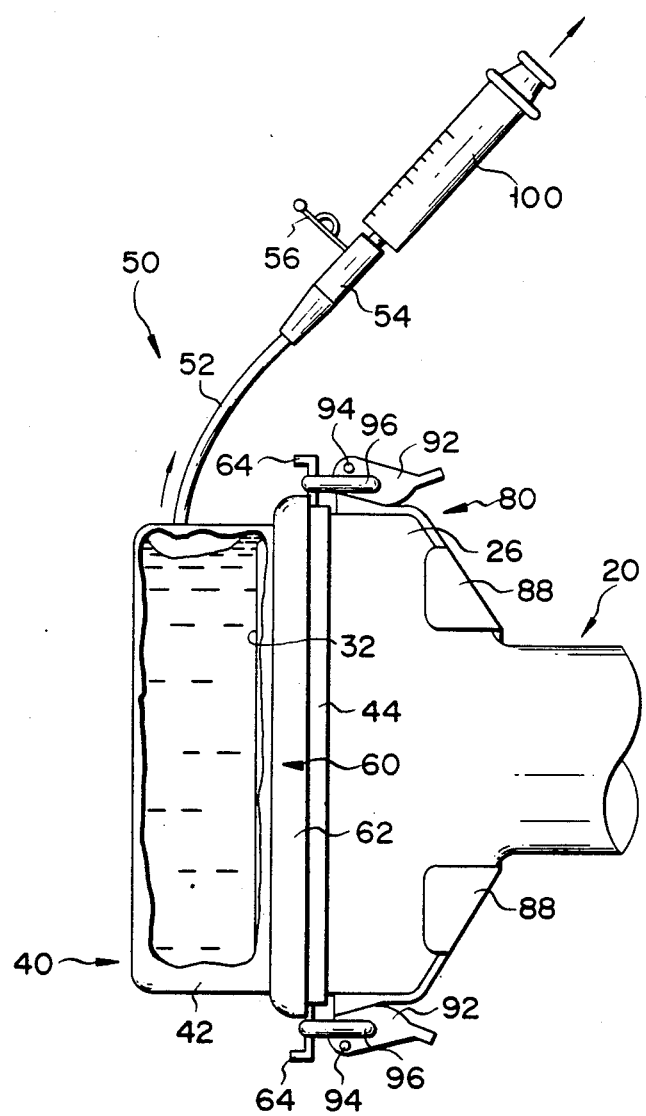

ULTRASONIC PROBE DEVICE

BACKGROUND OF THE INVENTION

The present invention relates to an ultrasonic probe device adapted for use in ultrasonic diagnosis and, more specifically, to an ultrasonic probe device which is capable of easily interposing a liquid acoustical medium between an ultrasonic transmitting/receiving face of a probe and the surface of a subject to be examined.

According to diagnostic techniques using ultrasonic probes, the movements of unborn babies, the defects or the internal organs of various portions of living bodies or organisms are observed as cross-sectional images by ultrasonic diagnoses. Generally, the surface of an organism is not even, but undulating. On the other hand, the ultrasonic transmitting/receiving face of a probe may be regarded as substantially even and rigid. Accordingly, it is hard to acoustically couple the probe and organism by bringing the ultrasonic transmitting/receiving face into contact with the organism's surface. Thus, in some cases, it is impossible to send ultrasonic waves into the organism to detect ultrasonic echoes therefrom.

Thus, a method has been proposed in which water, whose acoustical characteristics resemble that of the organism, is contained in a water bag made of, e.g., vinyl, with the water bag being interposed between the probe and the organism, so that the probe and the organism with an irregular surface shape are acoustically coupled by means of the water, which serves as an acoustical medium. In conventional ultrasonic diagnosis, however, a filled water bag, attached to a device under the probe, is placed on the regions of the human body to be examined, and the probe then performs the scanning operation. Not only is this device bulky, but the device for placing the water bag on the region to be examined is also large. Thus, the device is low in operating efficiency and requires a good deal of space.

In some ultrasonic probe devices, the water bag is attached directly to the probe. In these devices, however, the watertightness between the water bag and probe is not satisfactory, so that water is liable to leak, and operating efficiency is poor. Alternatively, the probe may be used singly, without being combined with the water bag. In the prior art ultrasonic probe device, however, it is not easy to attach and detach the water bag to and from the probe. Moreover, it is hard to pour water into the water bag or remove air bubbles therefrom. The probe and a living body may be coupled acoustically by interposing therebetween a filled, watertight rubber or vinyl bag. In this case, ultrasonic waves pass the rubber or vinyl sheet wall of the water bag twice. Therefore, the ultrasonic waves are greatly attenuated by the sheet wall.

SUMMARY OF THE INVENTION

One object of the present invention is to provide an ultrasonic probe device facilitating the attachment of a liquid bag to a probe, or the detachment thereof from the probe.

Another object of the invention is to provide an ultrasonic probe device accommodating the liquid-tight attachment of a liquid bag to a probe.

Still another object of the invention is to provide an ultrasonic probe device capable of easily and speedily pouring liquid acoustical medium into a liquid bag, and removing air therefrom.

A further object of the invention is to provide an ultrasonic probe device capable of the ultrasonic diagnoses of various parts of a subject to be examined with the reduced attenuation of ultrasonic waves.

According to the present invention, an ultrasonic probe device is provided comprising a probe including a case having lateral faces and an ultrasonic transmitting/receiving face with at least one transmitting/receiving element contained in the case capable of transmitting and receiving ultrasonic waves. The case has a probe engaging portion on the lateral faces thereof. A liquid bag includes a container portion for containing a liquid acoustical medium, and a bag engaging portion composed of an elastic material so adapted as to engage with the probe engaging portion of the case. A fitting member includes an opening in which the container portion is fitted and a press portion on the periphery of the opening. The press portion has a shape to match the bag engaging portion. A clamp member clamps the fitting member against the probe engaging portion in such a manner that the container portion is fitted into the opening, and the press portion engages the probe engaging portion with the bag engaging portion lying therebetween.

According to the invention, the liquid bag is attached to the probe by holding the bag engaging portion under pressure between the probe engaging portion and the press portion. Thus, the liquid bag can securely be attached to the case of the probe in a liquid-tight manner. Also, the liquid bag can be easily and speedily attached to or detached from the probe by mounting or removing the fitting member. If a tube is attached to the container portion, feeding the liquid acoustic medium into the liquid bag and the removal of air therefrom may speedily be achieved with ease. Since the ultrasonic waves pass through the container portion only once, they attenuate only slightly. In cases where water, whose acoustical characteristics are similar to those of an organism, is contained as an acoustical medium in the liquid bag, reflection of the ultrasonic waves can be reduced by producing the container portion from a natural rubber, such as latex.

The ultrasonic probe device may be so constructed that the fitting member has a pair of hooked projections projecting from the press portion, the clamp member includes a main body capable of being retained on the case of the probe, and a pair of handles rockably attached to the main body and rockably fitted with retaining frames capable of engaging with the hooked projections, so that the sealing portion is held under pressure between the press portion and the step portion, as handles of the clamp member are rotated, causing the retaining frames to engage with the projections. Thus, the fitting member may be easily and speedily attached to the probe by merely rotating the handles. Moreover, the fitting member may be reliably and stably attached, so that there is not possibility of its coming off the probe during ultrasonic diagnosis.

BRIEF DESCRIPTION OF THE DRAWINGS

FIG. 10 is a partial sectional view illustrating the way the water bag is exhausted.

DETAILED DESCRIPTION OF THE PREFERRED EMBODIMENT

Figure 1:
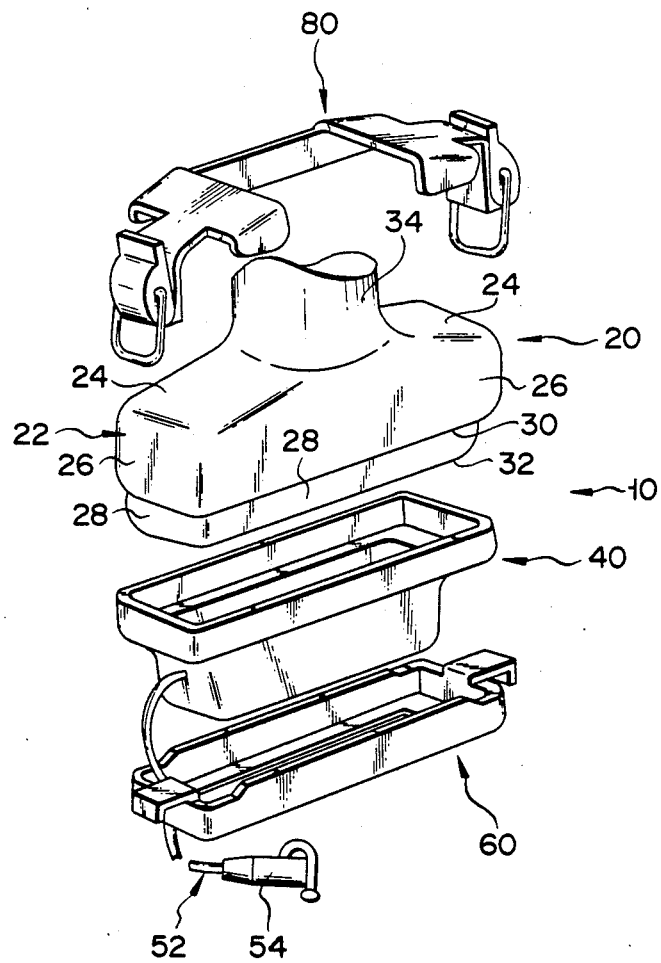
FIG. 1 is a disassembled perspective view of an ultrasonic probe device according to an embodiment of the present invention.
Figure 2:
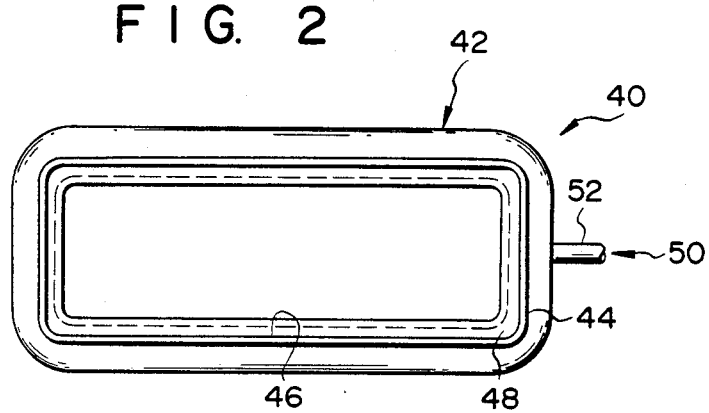
FIG. 2 is a plan view of a water bag used in the device of FIG. 1.
Figure 3:
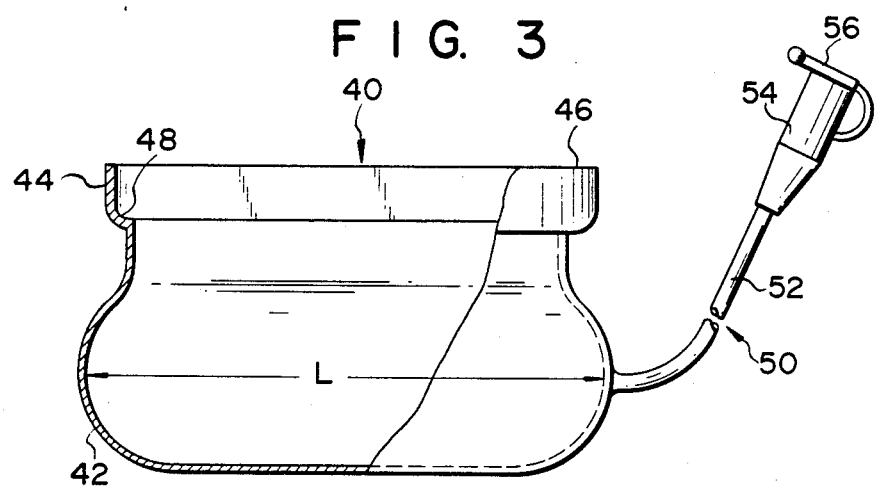
FIG. 3 is a front view of the water bag.

FIGS. 1 to 10 show an ultrasonic probe device according to one embodiment of the present invention. As shown in FIG. 1, a probe 20 has a case 22 substantially in the form of a rectangular parallelepiped, which hermetically contains therein a plurality of elements for transmitting and receiving ultrasonic waves. The case 22 has gently sloping shoulder faces 24, upper lateral faces 26, lower lateral faces 28, and a bottom face or ultrasonic transmitting/receiving face 32. A cable 34 is led out from between the two shoulder faces 24 which transmits electrical signals to the ultrasonic transmitting/receiving elements and sends the signals therefrom to a signal processing system (not shown). A step portion 30 is formed between the upper and lower lateral faces 26, 28 in a manner such that the peripheral edges of the upper lateral faces 26 are longer than those of the lower lateral faces 28. As the electrical signals are supplied to the ultrasonic transmitting/receiving elements, ultrasonic waves are transmitted from the ultrasonic transmitting/receiving face 32. When ultrasonic echoes are applied to the ultrasonic transmitting/receiving face 32, they are converted into electrical signals by the ultrasonic transmitting/receiving elements transmitted to the signal processing system through the cable 34.

A water bag 40 has a baglike container portion 42 for containing water which serves as an acoustical medium, and an engaging portion 44 which is integrally formed with respect to the container portion 42. The container portion 42 and engaging portion 44 are formed of a natural rubber, such as latex. Natural rubber is used since its acoustical characteristics resemble those of the human body, and since the water contained in such a container portion 42 produces less catoptric waves when ultrasonic waves are transmitted through the container portion 42. The wall of the container portion 42 is as thin as 0.1 to 0.2 mm, so that attenuation of the ultrasonic waves passing through the rubber sheet wall is minimized. The wall of the engaging portion 44 is relatively thick, being about 1 mm. Thus, the water bag 40 is strong enough to be attached to the probe 20, and watertightness between the water bag 40 and the probe 20 is ensured.

The peripheral edges of the container portion 42, adjoining the engaging portion 44, are as long as or a little shorter than those of the lower lateral faces 28 of the probe 20. The peripheral edges of an opening 46 of the engaging portion 44 are as long as or a little shorter than those of the upper lateral faces 26 of the probe 20. The engaging portion 44 has a sealing portion 48 where it meets the container portion 42, and whereby the water bag 40 is constricted like a neck. Alternatively, the whole water bag 40 may be formed with a uniform wall thickness. In this case, the shortage of the thickness of the engaging portion 44 must be filled by covering the engaging portion 44 with a ring about 1 mm thick, which is shaped in conformity with the engaging portion 44 (including the sealing portion 48). The material of this ring is not limited to natural rubber and may be selected from among any elastic materials, including synthetic rubber.

A water feeder 50 is attached to the flank of the container portion 42. This water feeder 50 includes a tube 52, attached to the flank of the container portion 42, for communicating with the space inside the container portion 42, and a connector 54 attached to the tube 52. As shown in FIG. 10, the connector 54 is so adapted as to be fitted with an injector 100, whereby water or air may be injected into or removed from the water bag 40.

Figure 4:
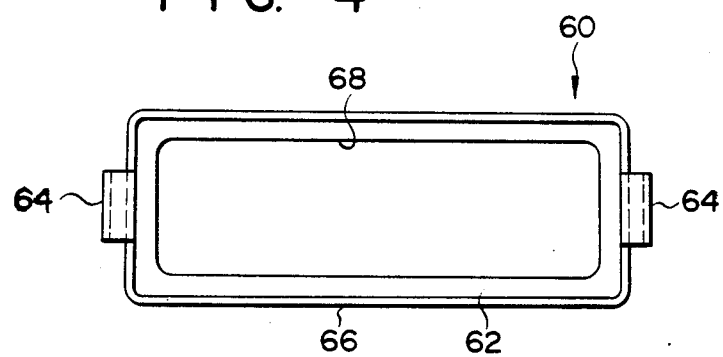
FIG. 4 is a plan view of a fitting member used in the device of FIG. 1.
Figure 5:
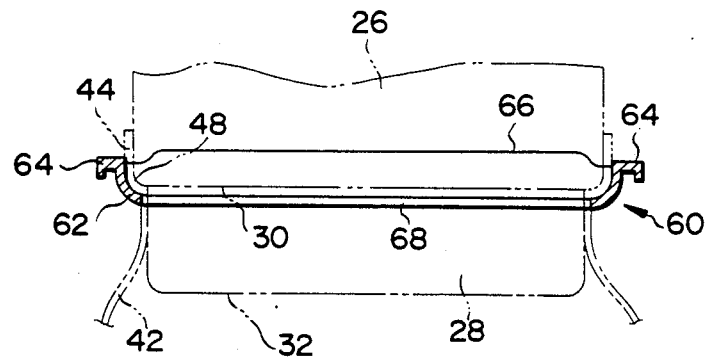
FIG. 5 is a vertical sectional view of the fitting member.

Referring now to FIGS. 4 and 5, a fitting member 60 may be described as follows. The fitting member 60 is in the form of a shallow tray, and includes a peripheral press portion 62 and a rectangular engaging opening 68. A hooked retaining projection 64 is formed on the central portion of each of the shorter sides of the press member 62. The press portion 62 has a shape that matches the step portion 30 of the probe 20 and the engaging portion 44 (including the sealing portion 48) of the water bag 40. Thus, the fitting member 60 may be fitted to the probe 20 in such a way that the press portion 62 engages the sealing portion 48 of the water bag 40, as indicated by the broken lines of FIG. 5, after putting the engaging portion 44 of the water bag 40 on the upper lateral faces 26 of the probe 20, so that the sealing portion 48 can mate with the step portion 30.

Figure 6:
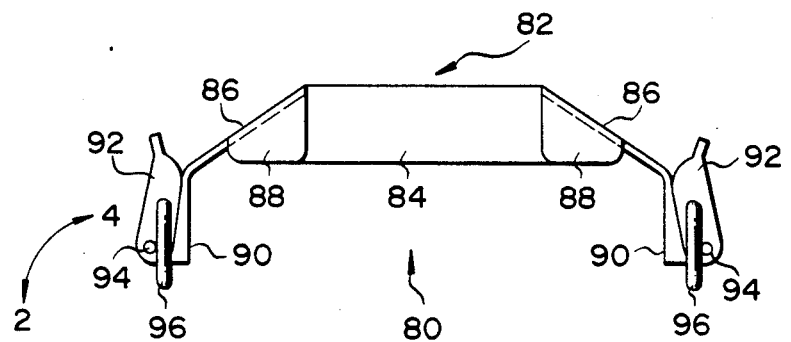
FIG. 6 is a front view of a clamp member used in the device of FIG. 1.
Figure 7:
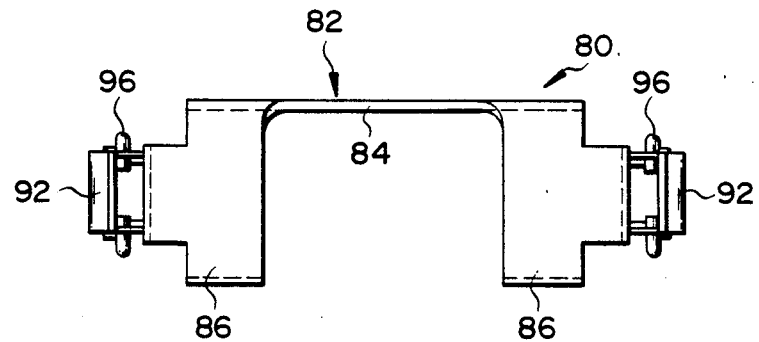
FIG. 7 is a plan view of the clamp member.
Figure 8:
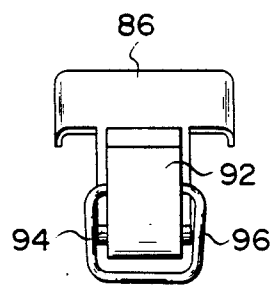
FIG. 8 is a side view of the clamp member.

Referring now to FIGS. 6, 7 and 8, a clamp member 80 may be described as follows. The main body 82 of the clamp member 80 has a shape which matches the shoulder faces 24 and upper lateral faces 26 of the probe 20. The main body 82 includes a lateral plate 84 which serves to engage one of the upper lateral faces 26 of the probe 20, shoulder plates 86 which serve to engage the shoulder faces 24 of the probe 20, partial lateral plates 88 which are continuous with the individual shoulder plates 86 and which face the lateral plate 84, and support portions 90 which are continuous with the individual shoulder plates 86. A handle 92 is rockably supported at one end of each of the support portions 90 by means of a pin 94. A retaining frame 96 is rockably attached to the substantially central portion of the handle 92. As the handles 92 rock in the directions of arrows 2 and 4 of FIG. 6 around their corresponding pins 94, the retaining frames 96 move up and down. When the handles 92 rock in the direction of arrow 4 and finally abut against their corresponding support portions 90, the portions of the retaining frames 96 attached to the handles 92 are located inside the pins 94, with respect to the facing direction of the support portions 90. The fitting member 60 and the clamp member 80 must be composed of highly rigid materials to clamp the engaging portion 44 of the water bag 40 between these member 60, 80. Preferably, therefore, these member 60, 80 should be composed of a cold-rolled steel sheet SPCC (JIS; ASTM A109-72), or other materials with high rigidity.

Figure 9:
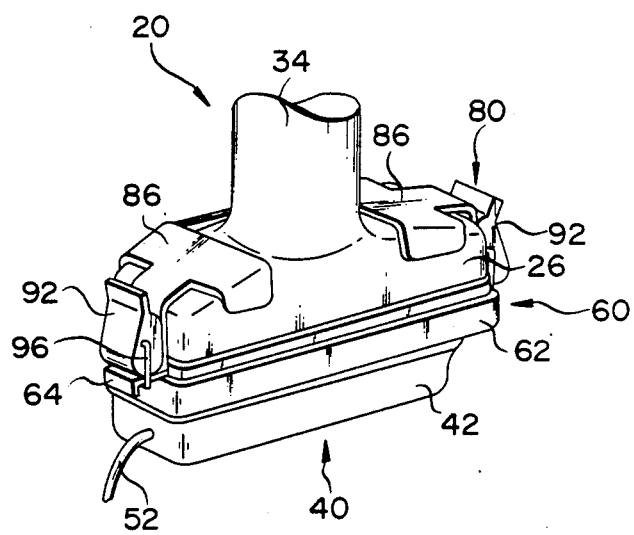
FIG. 9 is a perspective view of a probe fitted with the water bag.

Referring now to the disassembled and assembled views of FIGS. 1 and 9, the operation of the ultrasonic probe device 10 with the above-mentioned construction may be described as follows. First, the water bag 40 is attached to the probe 20. The engaging portion 44 of the water bag 40 is put on the upper lateral faces 26 of the probe 20, so that the sealing portion 48 of the water bag 40 engages with the step portion 30 of the probe 20. Then, the fitting member 60 is put on the water bag 40 so that the container portion 42 is fitted into the opening 68, and the press portion 62 engages with the step portion 30 of the probe 20 with the engaging portion 44 therebetween. Thereafter, the clamp member 80 is fitted to the shoulder faces 24 of the probe 20. The handles 92 are rotated in the direction of the arrow 2 of FIG. 6 to lower the retaining frames 96. After the retaining frames 96 are caused to engage their corresponding hooked projections 64, the handles 92 are rotated in the direction of the arrow 4 of FIG. 6, so as to abut against their corresponding support portions 90. As a result, the retaining frames 96 are lifted up so that the fitting member 60 and the clamp member 80 may clamp the water bag 40 against the probe 20. At this time, the retaining frames 96 are located on the inner sides of the clamp member 80, as compared with their corresponding pins 94, so that the handles 92 are settled in this state. The press portion 62 of the fitting member 60 presses the sealing portion 48 of the water bag 40 against the step portion 30 of the probe 20. In other words, the sealing portion 48 whose wall is somewhat thicker is held under pressure between the step portion 30 and the press portion 62. Thus, the water bag 40 is hermetically attached to the probe 20, and a sealed space is defined inside the water bag 40. Then, the injector 100 is attached to the connector 54, as shown in FIG. 10, and water is poured from the injector 100 into the water bag 40 through the tube 52. In this case, it is to be desired that the water feed should be started after squeezing the container portion 42 to remove as much air as possible. This should be done to avoid the production of air bubbles in the water poured into the water bag 40. If air bubbles remain in the water in the water bag 40, they may be sucked out by the injector 100, after turning the assembly in a manner such that the tube-connected portion of the container portion 42 faces upward, as shown in FIG. 10; or, they may be removed by squeezing the container portion 42. Water is further poured from the injector 100 into the water bag 40, to fill up the same 40. Thereafter, the injector 100 is disengaged from the connector 54, and the opening of the connector 54 is closed by a lid 56. The water bag 40 thus filled with the water is pressed against that part of the subject to be examined which requires diagnosis. Thus, the subject and the probe 20 are acoustically coupled by means of the water in the water bag 40 as an acoustic medium. When a signal is given to the ultrasonic transmitting-/receiving elements in the probe 20, ultrasonic waves from the ultrasonic transmitting/receiving face 32 of the probe 20 are propagated through the water, are passed through the natural rubber sheet wall of the container portion 42, and finally, reach the living body of the subject. Ultrasonic echoes reflected inside the living body pass through the sheet wall of the container portion 42, and are propagated through the water to reach the ultrasonic transmitting/receiving face 32. Thereupon, the ultrasonic echoes are converted into electrical signals by the transmitting/receiving elements, and are transmitted to the signal processing system (not shown). In this case, reflection of the ultrasonic waves by the inside faces of the container portion 42 of the water bag 40 may be reduced to improve the efficiency of the ultrasonic diagnosis by making the sheet wall distance L (see FIG. 3) of the container portion 42 longer than the ultrasonic transmitting region of the ultrasonic transmitting/receiving face 32.

It is to be understood that the present invention is not limited to the embodiment described above, since various changes and modifications may be effected therein by one skilled in the art, without departing from the scope or spirit of the invention. In particular, the acoustical medium is not limited to water, and may be suitably selected, according to the kind of subject to be examined. Also, the present invention may be applied to technologies other than ultrasonic diagnosis. In the above embodiment, the fitting member 60 and clamp member 80 are provided separately. Alternatively, however, the clamp member 80 may be rockably mounted on the fitting member 60, at the position of one of the hooked projections 64.

What is claimed is:

1. An ultrasonic probe device for examining a subject comprising:
   an ultrasonic probe including an impermeable bottom surface and a peripheral sealing surface surrounding said bottom surface, the ultrasonic probe further including ultrasonic transducer elements for transmitting ultrasonic waves and receiving echoes thereof through said bottom surface;
   an open-ended, impermeable, flexible bag including a peripheral sealing face adjacent the open end of said bag for engagement with said peripheral sealing surface of said ultrasonic probe, said impermeable bottom surface and said impermeable bag, when in sealed engagement, combining to define a liquid tight chamber for holding an acoustical liquid medium between said bottom surface and the inner surface of said bag;
   means for removably attaching said flexible bag to said probe and pressing said peripheral sealed surface of said probe and said peripheral sealed face of said bag into sealed engagement, said pressing means including a fitting member for engaging said bag proximate said peripheral sealing face and a clamp member for pressing the fitting member against said bag and toward said probe to place said peripheral sealing surface and said peripheral sealing face into sealed engagement; and
   means for selectively feeding an acoustical liquid medium to and from said liquid tight chambr and for selectively removing air from said chamber while said flexible bag is attached to said probe;
   whereby, when said bag and probe are attached, an acoustical liquid medium can be fed into said chamber, air can be removed from said chamber, the flexible bag holding an acoustical medium can be placed against a contoured surface of the subject, and ultrasonic waves and echoes can be transmitted to and from the subject through the liquid medium and the bottom of said bag.

2. The ultrasonic probe device of claim 1 wherein said feeding means includes a tube attached to said bag and communicating with said chamber and means for opening and closing said tube.

3. The ultrasonic probe device of claim 1 wherein said probe includes a stepped peripheral flange upon which said peripheral sealing surface is formed and the bag includes a complimentary stepped surface upon which said peripheral sealing face is formed.

4. The ultrasonic probe device of claim 1 wherein said fitting member includes a pair of hooked projections and said clamp member includes a main body for engagement with said probe and a pair of retaining finger means for engaging said hooked projections and pressing said fitting member toward said probe.

5. The ultrasonic probe device of claim 4 wherein said retaining finger means includes a pair of handles pivotally attached to said main body of said clamp member and a pair of retaining frames for engaging said hooked projections, one of each said frames being pivotally attached to a respective handle, whereby the retaining frames engage said hooked projections and press them toward said probe as the handles of said clamp member are rotated in one direction.

6. The ultrasonic probe device of claim 5 wherein said flexible bag is made of natural rubber and said liquid acoustical medium is water.

7. The ultrasonic probe device of claim 6 wherein the walls of said bag have a thickness of approximately 0.1–0.2 mm.

* * * * *